US00PP17701P3

(12) United States Plant Patent
Parfitt et al.

(10) Patent No.: US PP17,701 P3
(45) Date of Patent: May 8, 2007

(54) FEMALE PISTACHIO TREE NAMED 'LOST HILLS'

(50) Latin Name: *Pistacia vera*
Varietal Denomination: Lost Hills

(75) Inventors: Dan E. Parfitt, Davis, CA (US); Joseph Maranto, Bakersfield, CA (US); Craig E. Kallsen, Bakersfield, CA (US)

(73) Assignee: The Regents of the University of California, Oakland, CA (US)

( * ) Notice: Subject to any disclaimer, the term of this patent is extended or adjusted under 35 U.S.C. 154(b) by 93 days.

(21) Appl. No.: 11/086,616

(22) Filed: Mar. 21, 2005

(65) Prior Publication Data

US 2006/0212981 P1 Sep. 21, 2006

(51) Int. Cl.
*A01H 5/00* (2006.01)

(52) U.S. Cl. ..... Plt./152
(58) Field of Classification Search ..... Plt./152
See application file for complete search history.

(56) References Cited

PUBLICATIONS

U.S. Appl. No. 11/086,170, Parfitt et al.
U.S. Appl. No. 11/085,894, Parfitt et al.
Parfitt, D.E. et al. (1993) "Pistachio Cultivar Improvement: 1992," California Pistachio Industry, Annual Report, Crop Year 1992–93, p. 94.
Parfitt, D.E. et al. (1994) "Pistachio Cultivar Improvement: 1993," California Pistachio Industry, Annual Report, Crop Year 1993–94, pp. 98–99.
Parfitt, D.E. et al. (1995) "Pistachio Cultivar Improvement: 1994," California Pistachio Industry, Annual Report, Crop Year 1994–95, pp. 87–88.
Parfitt, D.E. et al. (1996) "Pistachio Cultivar Improvement: 1995," California Pistachio Industry, Annual Report, Crop Year 1995–96, pp. 90–98.
Parfitt, D.E. et al. (1997) "Pistachio Cultivar Improvement: 1996," California Pistachio Industry, Annual Report, Crop Year 1996–97, pp. 123–124.
Parfitt, D.E. et al. (1998) "Pistachio Cultivar Improvement: 1997," California Pistachio Industry, Annual Report, Crop Year 1997–98, pp. 134–142.
Parfitt, D.E. et al. (1999) "Pistachio Cultivar Improvement: 1998," California Pistachio Commission, 1998/99, Production Research Reports, pp. 230–279.
Parfitt, D.E. et al. (2000) "Pistachio Cultivar Improvement: 2000," California Pistachio Commission, 2000, Production Research Reports, pp. 303–304.
Parfitt, Dan E. et al. (1991) "Pistachio Cultivar Improvement—1990," California Pistachio Industry, Annual Report, Crop Year 1990–91, pp. 118–119.
Parfitt, Dan E. et al. (1992) "Pistachio Cultivar Improvement—1991," California Pistachio Industry, Annual Report, Crop Year 1991–92, pp. 163–164.
Parfitt, Dan E. et al. (1999) "Pistachio Cultivar Improvement: 1998," California Pistachio Industry, Annual Report, Crop Year 1998–1999, pp. 113–112.
Parfitt, Dan E. et al. (2000) "Pistachio Cultivar Improvement 1999," California Pistachio Industry, Annual Report, Crop Year 1999–2000, pp. 104–105.
Parfitt, Dan E. et al. (2001) "Pistachio Cultivar Improvement: 2000," California Pistachio Industry, Annual Report, Crop Year 2000–2001, pp. 141–142.

*Primary Examiner*—Kent Bell
*Assistant Examiner*—June Hwu
(74) *Attorney, Agent, or Firm*—Morrison & Foerster LLP

(57) ABSTRACT

A new and distinct variety of pistachio tree denominated 'Lost Hills' is described. This selections most significant advantage is the superior size and appearance of the in-shell nut. The variety is less chilling sensitive than 'Kerman' which improves uniformity of foliation, bloom, nut set, nut fill and uniformity of nut maturity at harvest.

11 Drawing Sheets

Botanical/commercial classification: (*Pistacia vera*)/new Pistachio variety.
Variety denomination: 'Lost Hills'.

BACKGROUND OF THE INVENTION

The present invention relates to a new and distinct variety of Pistachio tree *Pistacia vera* which has been denominated varietally as 'Lost Hills,' and more particularly to such a pistachio tree which has a harvest date of four to sixteen days earlier than the industry standard pistachio tree variety 'Kerman'.

Its novel features include an earlier harvest than 'Kerman', an individual nut size larger than 'Kerman' and the percentage of split nuts greater than 'Kerman'. The earlier harvest date will permit growers to extend their harvest period and reduce competition for scarce harvesting resources and will permit harvest in northern areas of the state before fall rains which can promote disease. The cultivar requires less chilling for dormancy than 'Kerman', which improves uniformity of foliation, bloom, pollination, nut filling and nut maturity at harvest in years with insufficient chilling for 'Kerman'.

SUMMARY OF THE INVENTION

It was found that the new cultivar exhibits the following combination of characteristics as compared to 'Kerman', the industry standard: a)This cultivar produced 26% higher grower paid yield than 'Kerman', the primary cultivar grown on a commercial basis in California (<95% of the crop), totaled across all 3 years and equal to 'Kerman' in 2004; b) Nut size is on average larger than 'Kerman' and weight is similar; c) Percent splits were consistently higher than 'Kerman', especially in 2003; d) Flowering and harvest are 2 to 4 weeks earlier than 'Kerman'. This earlier harvest date is important as it permits growers to more efficiently use their equipment and labor by spreading the harvest period across 6 weeks, rather than the current 3 week harvest period. Fruit ripening is also more uniform than was observed for 'Kerman'; e) Earlier harvest resulted in significantly less naval orangeworm damage (0.3% vs. 9.3%). This is an important characteristic since nut damage on the tree is associated with aflatoxin contamination; and f) 'Lost Hills' buds were about 1 mm longer than 'Kerman' buds.

'Lost Hills' has been asexually reproduced in Kern County, Calif. and Madera County, Calif. The cultivar was propagated from buds, inserted into both 'PG-1' and 'UCB1' rootstocks (budded onto). All of the cultivars are present at field locations in Kern Co. and Madera Co. (test plots). In addition 2 trees of each have been budded on 'UCB1' rootstocks in pots at Davis, Calif. for planting into the field this spring. In addition Lost Hills is grafted onto 'UCB1' rootstock in the field at the Wolfskill experimental farm near Winters, Calif. at row 4, trees 11A and B.

DETAILED BOTANICAL DESCRIPTION

The following description describes the key characteristics of a new female pistachio cultivar named 'Lost Hills' as well as reference to the standard pistachio cultivar 'Kerman' in California.

The Royal Horticultural Society color chart from 1986 is used in the identification of color. Also, common color terms are to be accorded their ordinary dictionary significance.

The cross: The cross that produced 'Lost Hills' was originally made in 1990, and the original seedling was planted at a research plot in 1991 near Bakersfield, Calif. The cross was made between a *Pistacia vera* female '2-35', located in Kern County and propagated from wood supplied to Joseph Maranto from a plot in California in 1985, and a *Pistacia vera* male 'ES#6' originally from Chico, Calif. ES#6 is no longer available. This selection from the cross was designated as B19-12. Field notes on its performance were taken from 1994 to 1999. Buds from this seedling tree were budded to rootstocks planted in August 1997 in an advanced selection trial in a plot near Lost Hills, Calif. Each plant selection is represented by 2 replicates of 10 trees grafted to 'UCB1' rootstock and 10 trees grafted to 'PG-1' rootstock per replicate. They first flowered in 2000. Performance data was taken in 2002, 2003, and 2004. Nursery rootstock trees were budded with this selection in 1997 and were used to plant a second advanced selection trial in Madera County north of Fresno in September 1999. Each plant selection is represented by two replicates of 5 trees grafted to 'UCB1' and 5 trees grafted to 'PG-1' per replicate. This selection flowered and fruited in 2003. Performance data was taken in 2004. The cultivar is stable and no significant differences in morphological or phenological characteristics were observed when propagated on rootstocks.

Tree vigor: The tree is of average size for a pistachio, based on observation of 7 year old trees. Grafted trees are about 3 m tall at 7 years with a spread equal to the height. Trunk diameters are 10 to 15 cm.

Figure 2:
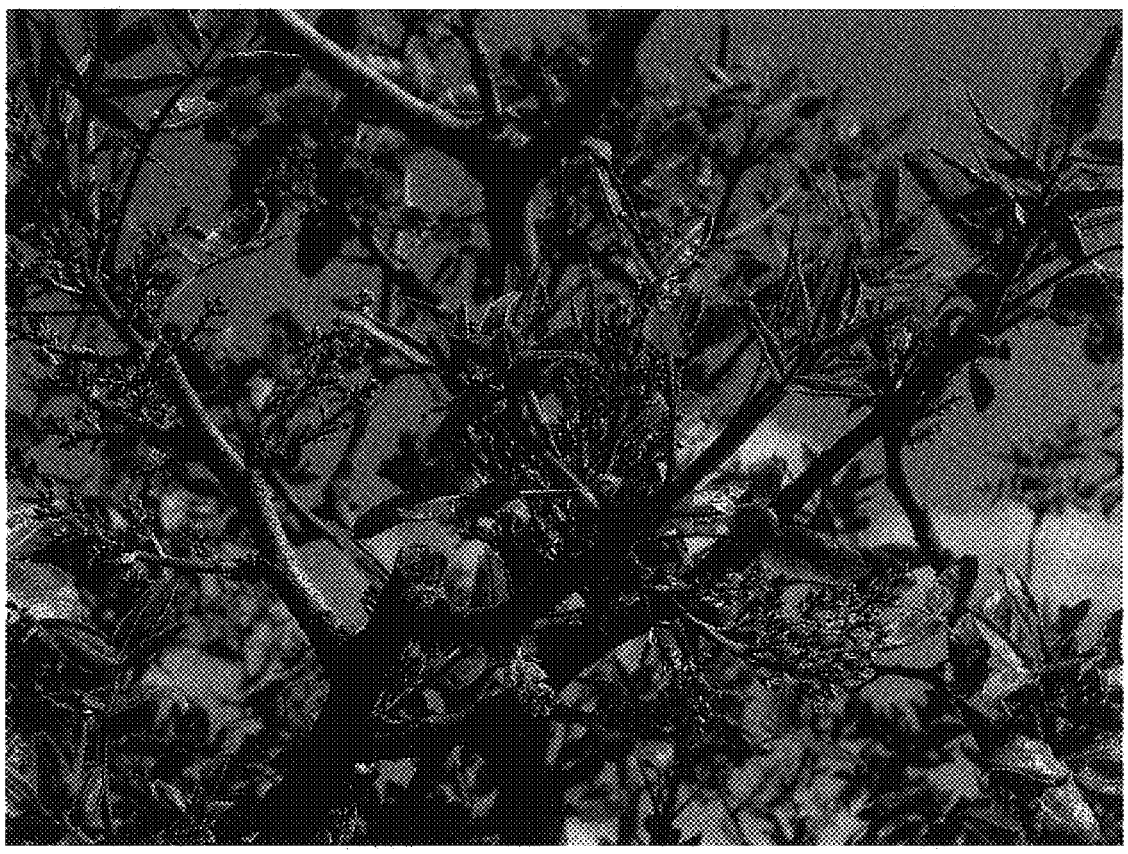
FIG. 2. 'Lost Hills' flowers—Mar. 31, 2004. About one week ahead of 'Kerman', flowers have set, end of bloom period.
Figure 6:
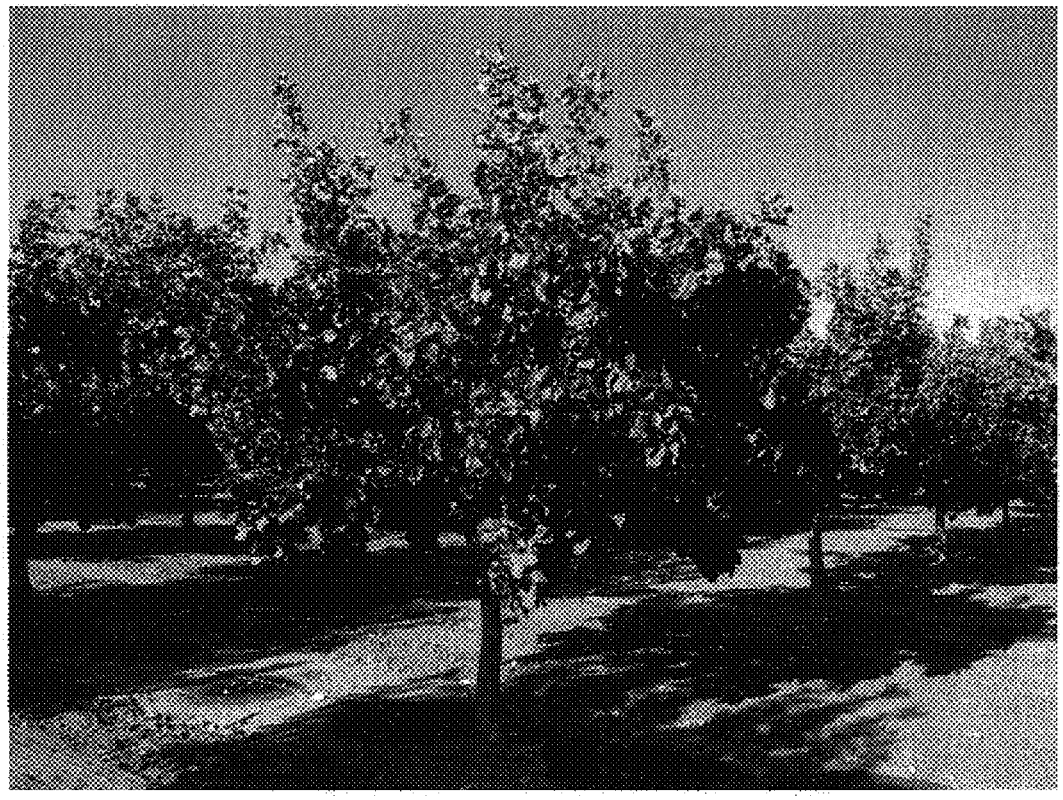
FIG. 6. Picture of 'Lost Hills' trees at the Bakersfield test plot in 2003.

Tree structure: 'Lost Hills' has tree structure and branching habit typical for *Pistacia vera* L. Branch angles are broad, ranging from 80 to 90 degrees for both scaffold and lateral branches. Distribution of scaffold and lateral branches are a function of pruning and training activities which are practiced intensively during the first three years of growth (FIGS. 2 and 6).

Bark: 'Lost Hills' bark color was identical to the bark color of 'Kerman', specifically RHS 202D (grey).

Figure 13:
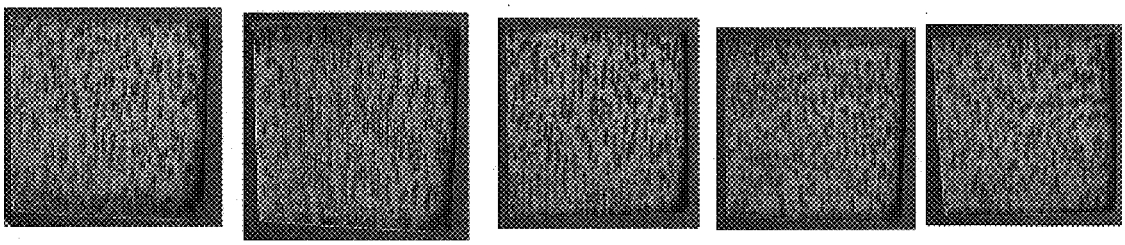
FIG. 13. Lenticel pictures from each of 5 trees for 'Kerman' and 'Lost Hills'. The areas shown are 25 sq. cm, 5 cm on each side.
Figure 13:
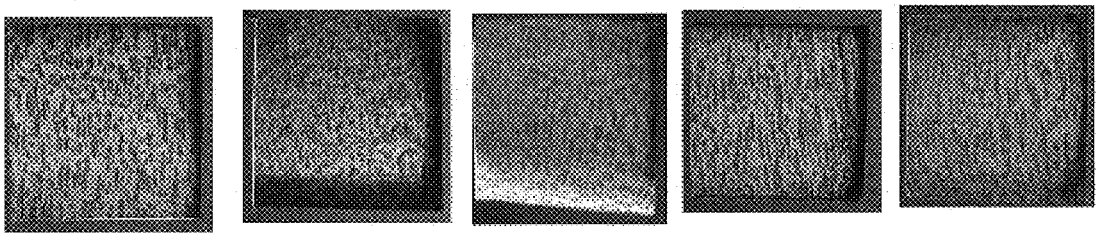

Trunk lenticels: Close up photo evaluation of trunk lenticels was undertaken. No clear consistent differences in pattern were observed between the 2 cultivars. The distribution and physical characteristics of lenticels for 'Lost Hills' appeared to be quite variable, perhaps more so than for 'Kerman'. FIG. 13 shows sample pictures from 5 trees of each cultivar. The area shown is 5 cm×5 cm. 'Kerman' lenticels appear to be distinctly shorter and are more widely spaced on the bark, both horizontally and vertically. The color of the 'Lost Hills' lenticels ranged from RHS 172C (grey orange) to RHS 199B-C (grey brown) as compared to 'Kerman', for which the color of the lenticels was RHS 172D. The width of the lenticels of 'Lost Hills' ranged from 1 to 2 mm, with an average of 1.5 mm. The width of the lenticels of 'Kerman' ranged from 1 to 2 mm, an average of 1.8 to 2.0 mm. The height of the lenticels from both 'Lost Hills' and 'Kerman' was an average of 1 mm.

Flower buds: Bud size analysis for 'Lost Hills' and 'Kerman' was limited to bud length, since this was the only characteristic that seemed to be different between the cultivars. The buds were much thinner than for the males, making width measurements problematic. 10 buds per tree were measured for each of 5 trees. Within tree differences were not found to be highly significant, so data for each cultivar was bulked (eg. 50 buds per cv) and analyzed using a completely random design. As can be seen from the data analysis, bud length differences were highly significant. 'Lost Hills' buds were about 1 mm longer than 'Kerman' buds. (Tables 1 and 2). The color of the emerging inflorescence for 'Lost Hills' was RHS 145B while the color of the emerging inflorescence for 'Kerman' was RHS 145C (yellow-green).

TABLE 1

ANOVA Table for bud I (mm)

| | DF | Sum of Squares | Mean Square | F-Value | P-Value | Lambda | Power |
|---|---|---|---|---|---|---|---|
| Cultivar | 2 | 25.473 | 12.736 | 25.503 | <.0001 | 51.007 | 1.000 |
| Residual | 147 | 73.411 | .499 | | | | |

Means Table for bud I (mm)
Effect: Cultivar

| | Count | Mean | Std. Dev. | Std. Err. |
|---|---|---|---|---|
| Golden Hills | 50 | 8.340 | .626 | .089 |
| Kerman | 50 | 7.476 | .643 | .091 |
| Lost Hills | 50 | 8.360 | .832 | .118 |

TABLE 2

Effect: Cultivar
Significance Level: 5%

| | Mean Diff. | Crit. Diff. | P-Value | |
|---|---|---|---|---|
| **Fisher's PLSD for bud I (mm)** | | | | |
| Golden Hills, Kerman | .864 | .279 | <.0001 | S |
| Golden Hills, Lost Hills | <.020 | .279 | .8877 | |
| Kerman, Lost Hills | <.884 | .279 | <.0001 | S |
| **Scheffe for bud I (mm)** | | | | |
| Golden Hills, Kerman | .864 | .350 | <.0001 | S |
| Golden Hills, Lost Hills | <.020 | .350 | .9900 | |
| Kerman, Lost Hills | <.884 | .350 | <.0001 | S |

Figure 1:
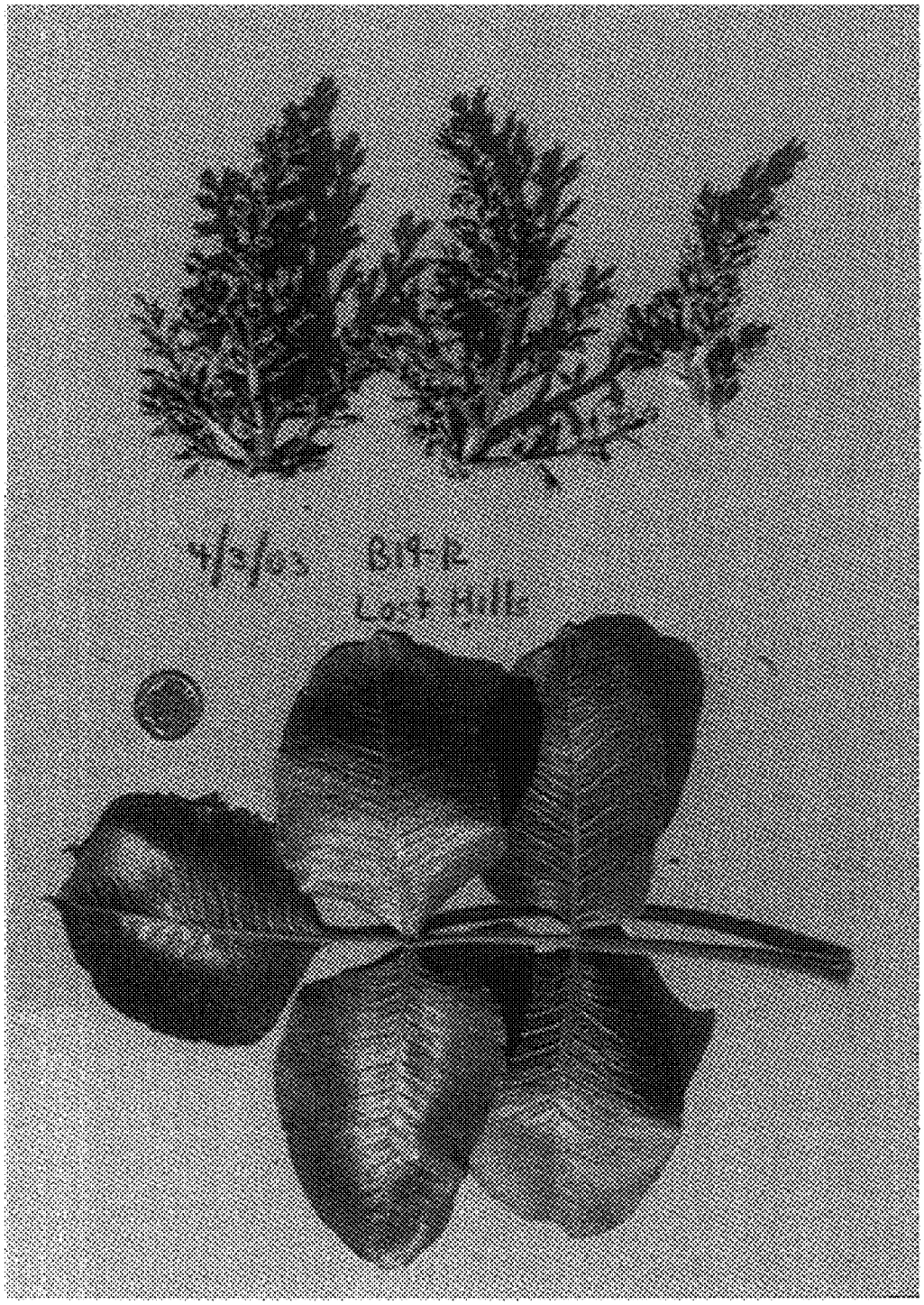
FIG. 1. Flowers and leaves from grafted trees at the Bakersfield test plot in 2003.
Figure 3:
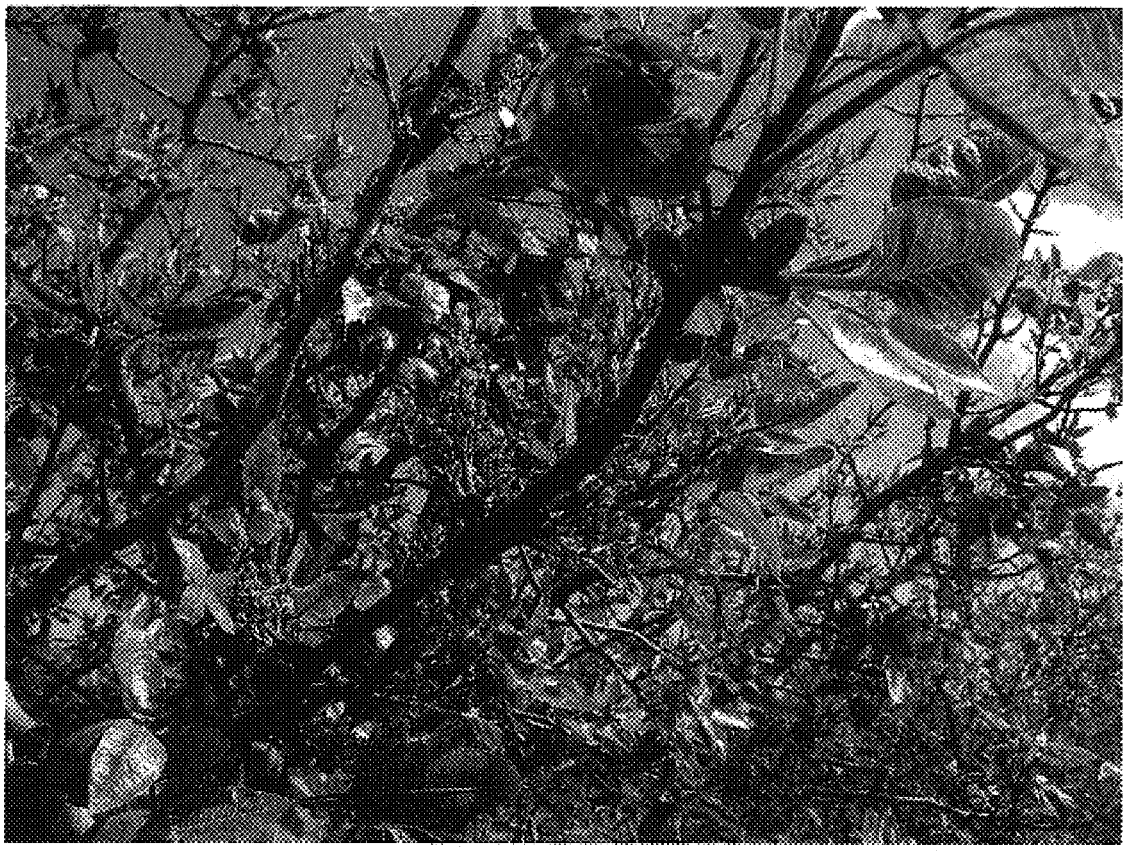
FIG. 3. 'Kerman' flowers—Mar. 31, 2004, mid-bloom. Note that leafing is more advanced than for 'Lost Hills' even though flowering is later.
Figure 4:
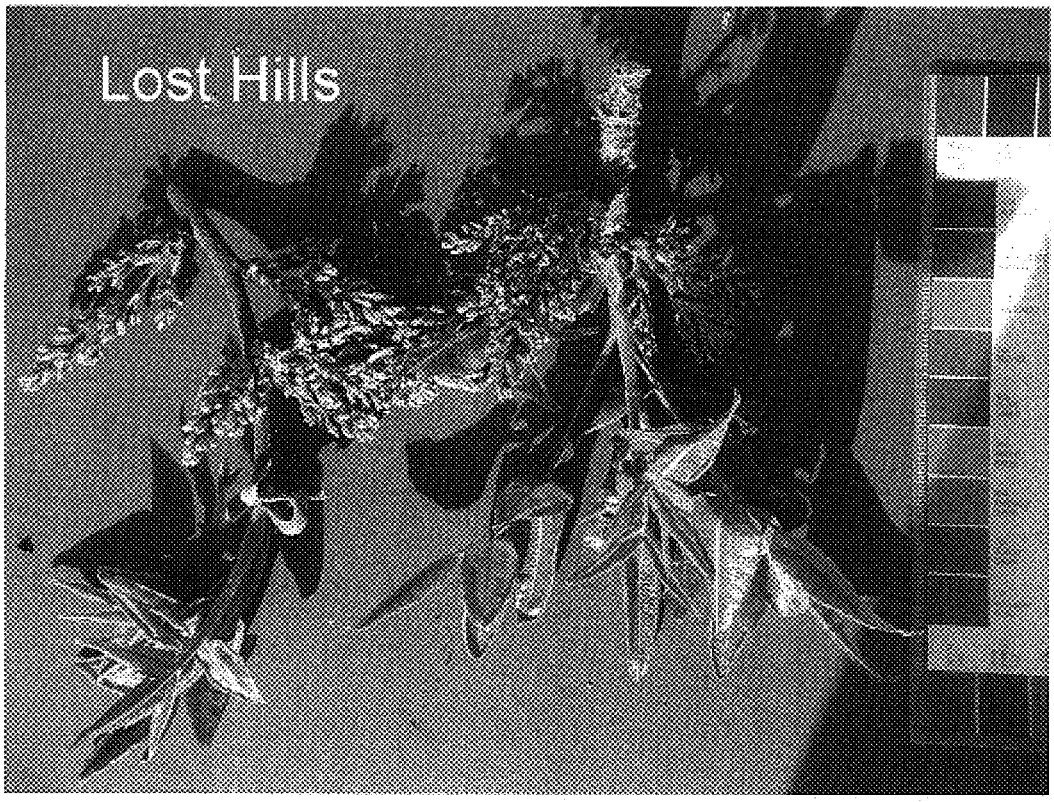
FIG. 4. Comparisons of 'Lost Hills' and 'Kerman' leaves and flowers—Mar. 31, 2004.
Figure 4:
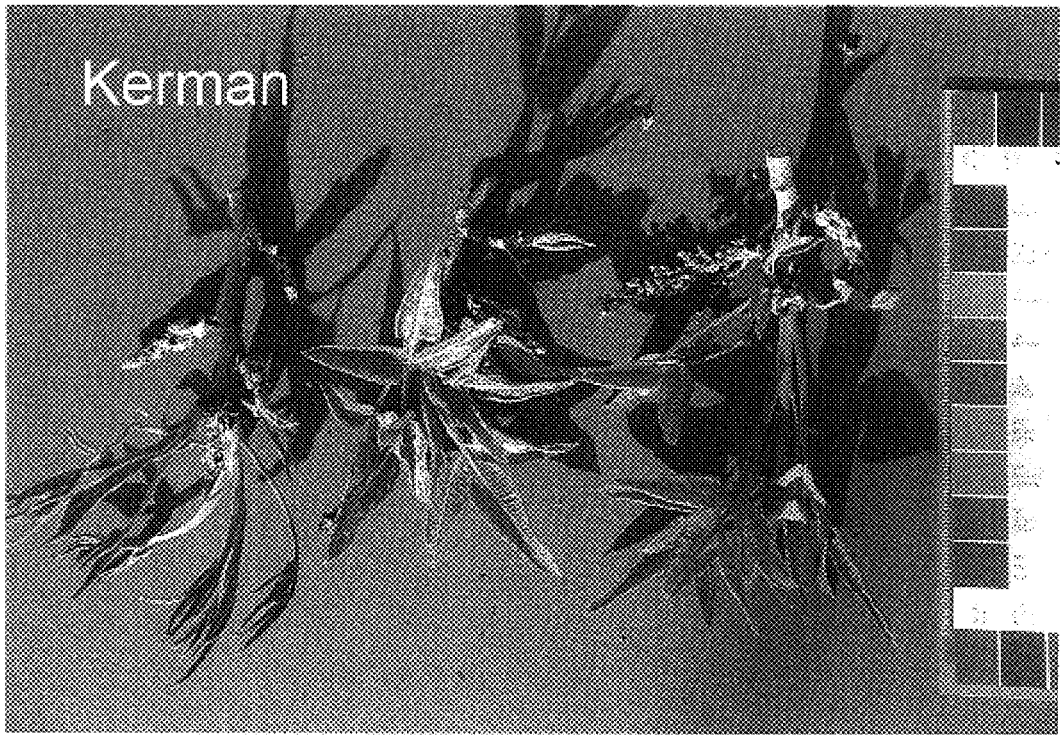

Inflorescences: Female inflorescences are born laterally alternately on branches, rarely as terminal buds. They are located on one year old wood. The flower buds form a branched compound inflorescence of the panicle form. Individual flowers are about 1 mm in size. All flowers are female. The panicles are 5 to 8 cm long with considerable variation in size. The panicles become more extended as flowering progresses. Flowers become receptive from the base to the tip of the panicle, and the total period of receptivity may spans a 3 week period, depending on weather conditions during individual seasons. Flowers are pale green (RHS 144C) as are the supporting structures of the panicles (FIGS. 1, 2 and 4). Comparisons with 'Kerman' are provided in FIGS. 3 and 4.

Flowering date:

Data from seedling test plot in Kern County, Calif.:

1996: For 'Lost Hills'—Apr. 8, 1996

1997: For 'Lost Hills'—first flowering Apr. 22, 1997 to Apr. 28, 1997, peak flowering Apr. 29, 1997 to May 5, 1997, last flowering Apr. 29, 1997 to May 5, 1997; for 'Kerman'—first flowering Apr. 22, 1997 to Apr. 28, 1997, peak flowering Apr. 29, 1997 to May 5, 1997, last flowering—May 6, 1997 to May 13, 1997

1998: For 'Lost Hills'—first flowering Apr. 4, 1998 to Apr. 11, 1998, peak flowering Apr. 12, 1998 to Apr. 19, 1998, last flowering Apr. 20, 1998 to Apr. 27, 1998; for 'Kerman'—first flowering Apr. 20, 1998 to Apr. 27, 1998, peak flowering Apr. 28, 1998 to May 5, 1998, last flowering May 6, 1998 to May 13, 1998

1999: For 'Lost Hills'—first flowering Mar. 13, 1999 to Mar. 16, 1999, peak flowering Mar. 17, 1999 to Mar. 21, 1999, last flowering Mar. 21, 1999 to Mar. 26, 1999

2000: For 'Lost Hills'—first flowering Apr. 8, 2000 to Apr. 13, 2000

Data from grafted test plot in Kern County: Trees were grafted on either 'UCB1' or 'Pioneer Gold-1' rootstocks. Visits to the two experimental sites were made at intervals of three to four days through the bloom period. In 2004 ($8^{th}$ year since grafting), a bloom-rating of 1 through 6 was used with 1=dormant; 2=early bloom, 3=mid bloom, 4=full bloom and 5=late bloom. Bloom evaluation is subjective; the number of individual flowers in bloom within an inflorescence varies, as does the degree of flowering at different locations along a branch. Full bloom was an estimate of when the maximum number of receptive stigmas were present on the tree. On Mar. 25, 2004 'Lost Hills' was at full or mid bloom (3.3), 'Kerman' was just beginning to break buds (1.5).

Leaves: The leaves are single parapinnate compound leaves with an average number of leaflets of 3 or 5. The apex of the leaflet blades is obtuse to cuspidate, and the leaflet base is rounded. The leaflet margins are entire to slightly crenate. The leaflets are oval to ovate. The terminal leaflet appears mucronate in some situations. The leaflets are typically 3–5 cm wide and 4 to 7 cm long. The compound leaf is typically 10 to 15 cm long. There is a considerable variation in leaf and leaflet size depending on time of the season, position in the tree, and year. The width of a compound leaf ranges from 8 to 14 cm. The length of a compound leaf ranges from 10 to 15 cm. Margins of leaf blades are entire. Leaf surfaces are glabrous, smooth and waxy. The color of the upper and lower surfaces of the leaves ranges from light green (RHS 139B) at first emergence to dark green (RHS 139A) at maturity (RHS 136A to RHS 136A). FIGS. 1, 2, and 4). The upper surfaces of the leaves of 'Kerman' range from RHS 136A to RHS 139A at emergence to maturity (FIG. 4). The leaf vein and petiole of 'Lost Hills' are a light yellowish green in color (RHS149C to D). The petiole is 4 to 7 cm in length and the texture is smooth, with no wings.

Leafing date: 'Lost Hills' flowers significantly before 'Kerman', leafing tends to follow flowering, rather than being synchronous as with 'Kerman'.

1997: for 'Lost Hills'—first leafing Apr. 29, 1997 to May 5, 1997; for 'Kerman' Apr. 29, 1997 to May 5, 1997

1998: for 'Lost Hills'—first leafing Apr. 20, 1998 to Apr. 27, 1998; for 'Kerman' Apr. 20, 1998 to Apr. 27, 1998

1999: for 'Lost Hills'—first leafing Mar. 16, 1999 to Mar. 23, 1999

2000: for 'Lost Hills'—first leafing Apr. 8, 2000 to Apr. 13, 2000

Figure 5:
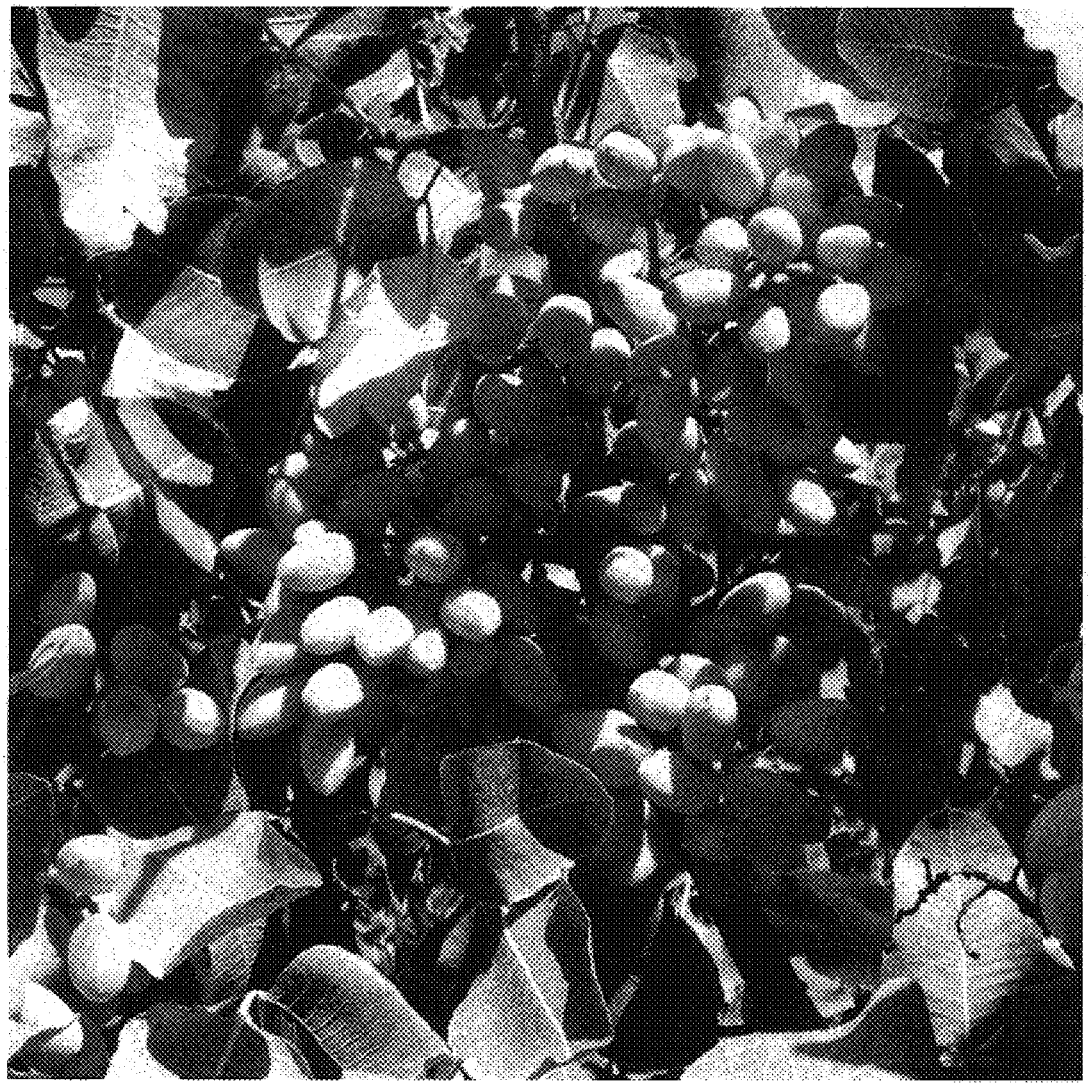
FIG. 5. Fruit clusters on 'Lost Hills' tree at Bakersfield plot, 2003.
Figure 7:
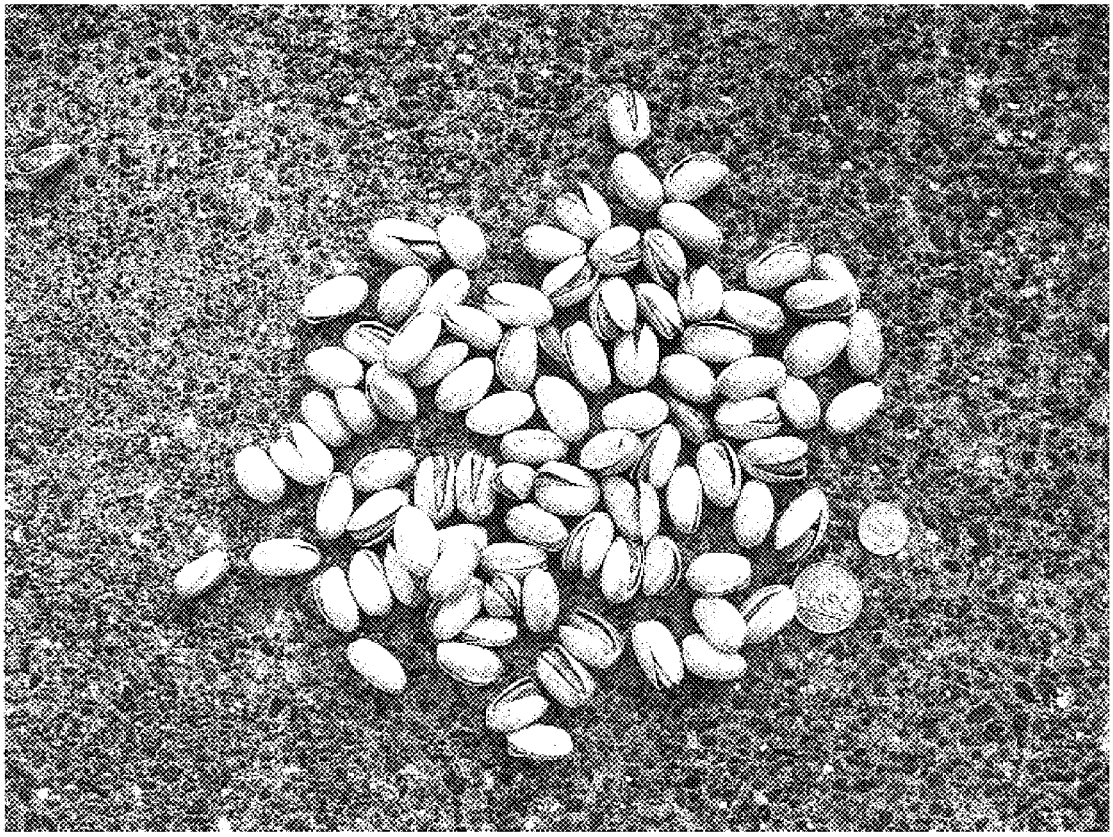
FIG. 7. Roasted seed harvested from 'Lost Hills' grafted trees in the Bakersfield plot, 2003.
Figure 8:
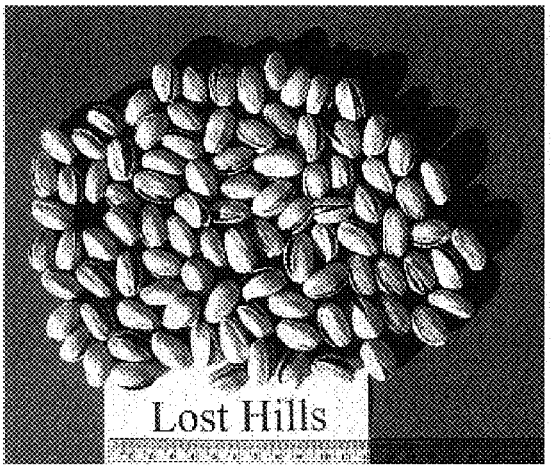
FIG. 8. 'Lost Hills' and 'Kerman' roasted nuts.
Figure 8:
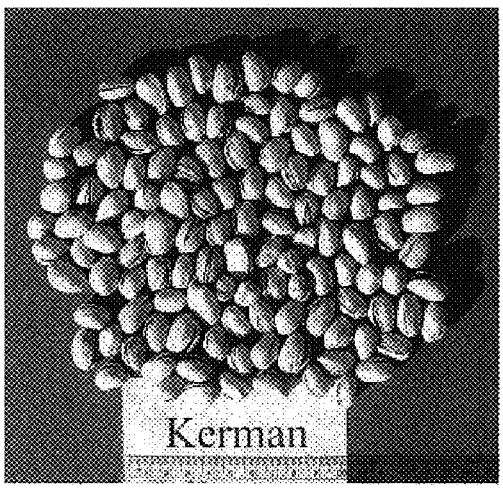
Figure 9:
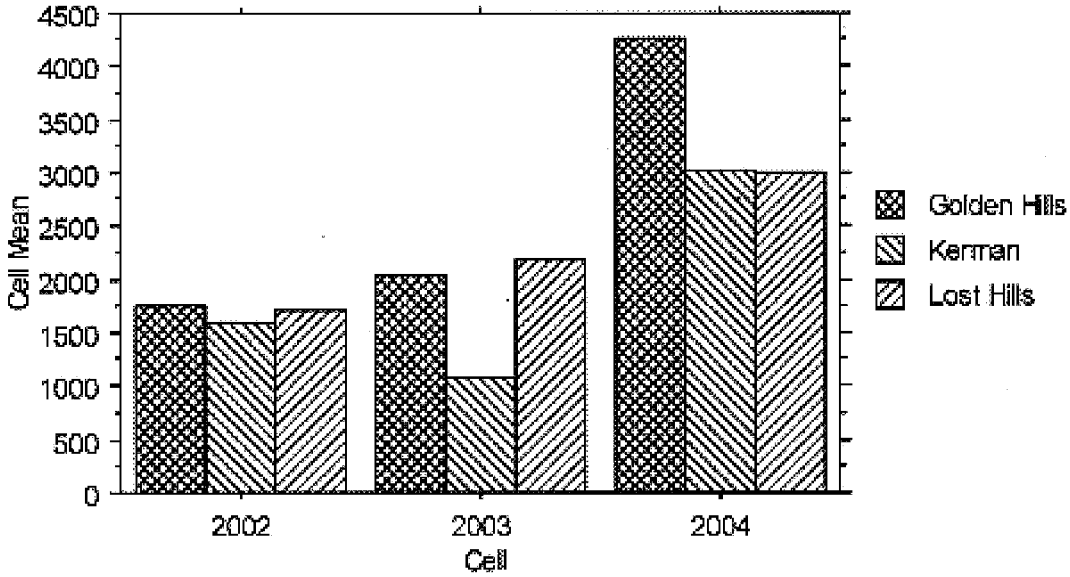
FIG. 9. Year by variety mean values for total yield (CCP assessed weight).
Figure 10:
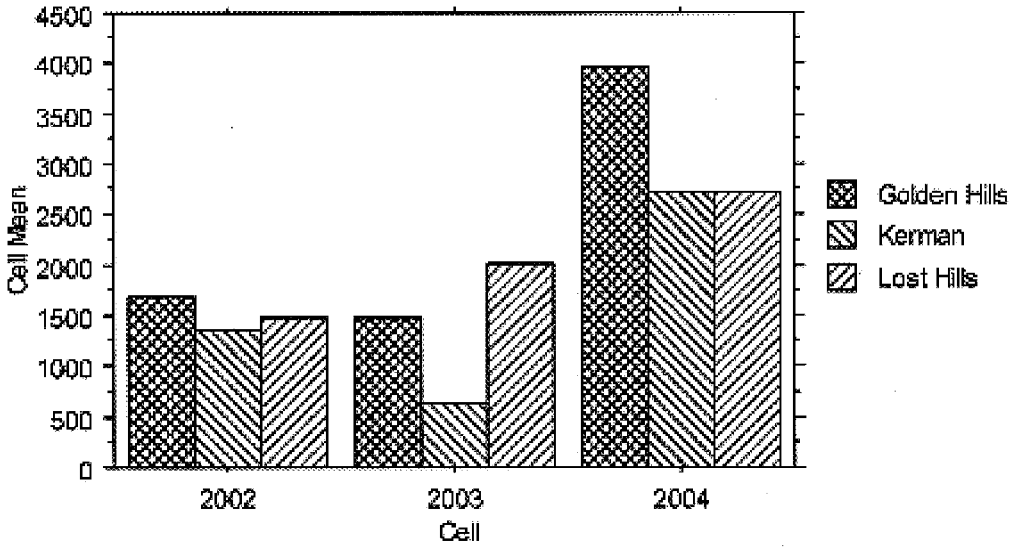
FIG. 10. Year by variety mean values for yield of split nuts.
Figure 11:
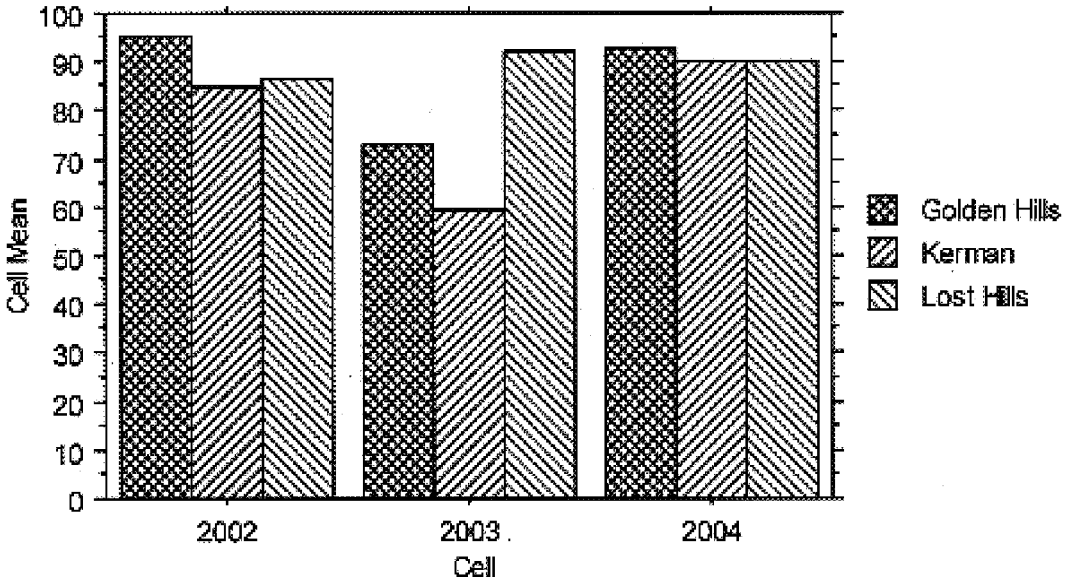
FIG. 11. Year by variety mean values for yield of % split nuts—untransformed data.
Figure 12:
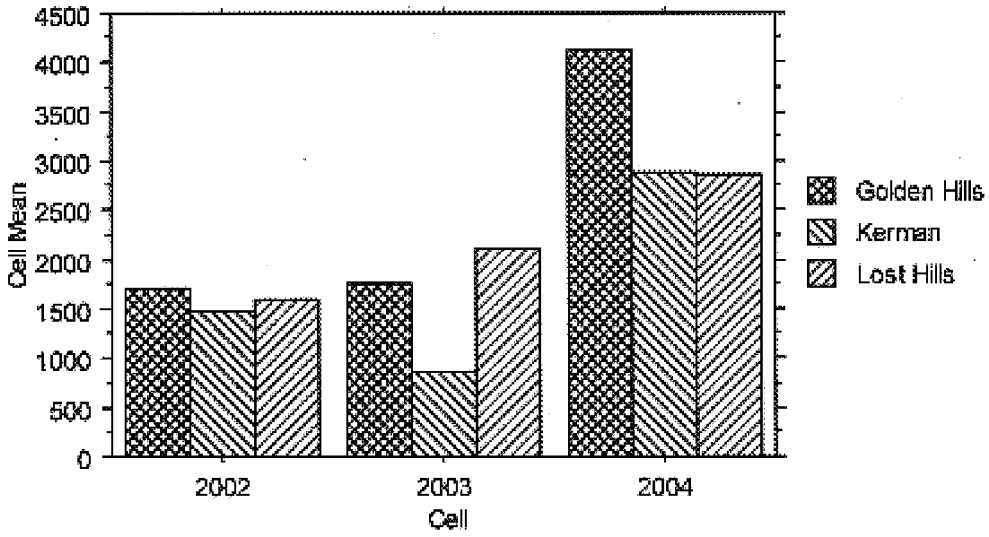
FIG. 12. Year by variety mean values for grower paid yield.

Nut description: Nuts are arranged in panicle clusters (FIG. 5). They are considered drupes. Most flowers abort so that 10 to 20 nuts per cluster remain. The color of the pellicle for 'Lost Hills' is grey shading to purple-red (RHS 201D). The pellicle is approximately 0.1 mm in thickness. Husk color gradually changes from a light green in late June to a creamy white color (RHS 8D to 11D) prior to harvest (FIG. 5). The surface texture of the hull is smooth and dull, with roughness approximately equivalent to 1000 grit sandpaper. The hull thickness ranges between 1 and 1.5 mm. Husks (exo-mesocarp) initially adhere tightly to the shell (endocarp) but become detached but intact at harvest. Past harvest the husks split, exposing the shell. Shells split midseason, usually 4 to 6 weeks prior to harvest. Some shells do not split, producing a nut with low economic value. This is an important commercial character. Blank nuts are formed when the embryo aborts but the shell and husk continue to develop. Blank nuts are commercially undesirable and do not contribute to yield. 'Lost Hills' produces a processed nut that is larger than 'Kerman' in size and similar in color. Nuts are oval, longer than wide with a round and rounded tip (FIG. 7). The shell suture is deep, extending from the tip almost to the base and is symmetrical. 'Kerman' nuts are noticeably shorter than 'Lost Hills' nuts (Table 3) and are less symmetrical (FIG. 8). Shell sutures are less symmetrical and a significant percentage of in-shell nuts have a flattened shape with longer shell sutures on one side, not typical for 'Lost Hills'. The color of the 'Lost Hills' kernel is green (RHS 144C), darker than the kernel of 'Kerman' (RHS 149D). The average kernel size is 2.02 cm in length, 1.06 cm in width, and 1.05 cm in depth. The form of the kernel is generally egg-shaped or ovate, narrowing toward the micropylar end. There is usually an offset depression near rhte stem end. The stem end of the kernel terminates in a dull point. The surface texture of the kernel is smooth, with surface wrinkles oriented in a linear manner from the stem end to the micropylar end. The average weight of the kernel is 0.68 grams. The flavor of the kernel is typical of pistachios, similar to 'Kerman', and is slightly sweet and nutty.

TABLE 3

Average individual nut length and width[1] of nuts for 'Lost Hills' and 'Kerman' on 'PG-1' rootstock from a test plot in northwestern Kern County from 2002 through 2004 (7th and 8th leaf).

| | nut length, mm | | nut width, mm | |
|---|---|---|---|---|
| Cultivar | 2003 | 2004 | 2003 | 2004 |
| 'Lost Hills' | 21.3 | 19.8 | 12.5 | 13.4 |
| 'Kerman' | 17.8 | 17.0 | 12.2 | 12.3 |

[1]In 2003 the values in the table were based on one 50 nut sample from each variety. In 2004 the values in the table were based on one 50 nut sample from each of the two replicates of each variety.

Split nuts as a percentage of total nuts (at Kern Co. location unless otherwise noted):

2002: 'Lost Hills'=86%; 'Kerman'=85%

2003: 'Lost Hills'=92%; 'Kerman'=60%

2004; 'Lost Hills'=90%; 'Kerman'=90%

2004 at Madera plot; 'Lost Hills'=74%; 'Kerman'=59%

Blank nut percentages (at Kern Co. location unless otherwise noted):

Cumulative 2002–2004: 'Lost Hills'=4.1%; 'Kerman'=24.2%

Harvest date: 'Lost Hills' matures 2 to 3 weeks earlier than 'Kerman' (Table 4). This is a valuable commercial character as it permits growers to better manage the harvest which otherwise occurs over a short time period. Delayed harvest can also result in high levels of insect (Naval Orangeworm) damage and associated aflatoxin contamination.

TABLE 4

Harvest dates for 'Lost Hills' and 'Kerman' on 'PG-1' rootstock from a test plot in northwestern Kern County from 2002 through 2004 (6th through 8th leaf).

| Cultivar | 2002[1] | 2003[1] | 2004 |
|---|---|---|---|
| 'Lost Hills' | September 4 | August 29 | August 25 |
| 'Kerman' | September 4 | September 19 | September 21 |

[1]Oil applied in February of 2002 and 2003 to promote earlier bloom in the surrounding orchard (and also in the test plot).

Insect damage: Cumulative insect damage on nuts was 0.3% for 'Lost Hills' and 9.3% for 'Kerman' from 2002 through 2004.

Additional harvest timing, yield and nut quality information (2002 and 2003) for 'Lost Hills' compared to 'Kerman' on PG-1 rootstock is shown below. The data from the Kern County Plot is from a different sampling than that shown below. (Table 19).

TABLE 19

| | 2002 | | 2003 | |
|---|---|---|---|---|
| Characteristic | 'Kerman' | 'Lost Hills' | 'Kerman' | 'Lost Hills' |
| nut yield (CPC weight) (5% moisture) , lbs/tree | 12.8 | 12.6 | 8.0 | 16.2 |
| split edible in-shell, lbs/tree | 10.0 | 10.9 | 4.7 | 14.9 |
| edible in-shell split percentage | 78 | 86 | 52 | 89 |
| loose shell and kernel percentage | 1 | 10 | 0 | 1 |
| closed shell percentage | 20 | 3 | 46 | 10 |
| blank nuts (no kernel) percentage | 7 | 2 | 6 | 4 |
| individual nut weight (grams) | 1.44 | 1.57 | 1.25 | 1.48 |
| approximate date ready for harvest | Sep. 4, 2002 | Sep. 1, 2002 | Sep. 16, 2003 | Aug. 29, 2003 |

Yield: 'Lost Hills' had yields, including grower paid yield (after non-split nuts and insect damaged nuts are accounted for), similar to 'Kerman', but significantly greater yields for 2002, a year with low chilling. Cumulative yields for 'Lost Hills' from 2002 through 2004 were 26% greater for 'Kerman', mostly due to improved performance in 2003. (FIGS. 8–12).

Total yield in lbs/acre:

2002: 'Lost Hills'=1708; 'Kerman'=1593

2003: 'Lost Hills'=2185; 'Kerman'=1081

2004: 'Lost Hills'=2998; 'Kerman'=3032

Yield of split nuts in lbs/acre:

2002: 'Lost Hills'=1474; 'Kerman'=1355

2003: 'Lost Hills'=2017; 'Kerman'=641

2004: 'Lost Hills'=2707; 'Kerman'=2725

Grower paid yield in lbs/acre:

2002: 'Lost Hills'=1591; 'Kerman'=1474

2003: 'Lost Hills'=2100; 'Kerman'=861

2004: 'Lost Hills'=2853; 'Kerman'=2875

Values for total yield, inshell yield, and grower paid yield are presented in Table 5.

TABLE 5

Cumulative nut yields[1] for 'Lost Hills' and 'Kerman' on 'PG-1' rootstock from a test plot in northwestern Kern County from 2002 through 2004 (6th through 8th leaf).

| Cultivar | CPC assessed weight, lbs./acre | Edible split inshell nuts, lbs./acre | Grower-paid yield[2], lbs./acre |
|---|---|---|---|
| 'Lost Hills' | 6891 | 6198 | 6543 |
| 'Kerman' | 5707 | 4721 | 5211 |

[1]Yields based on two replications of 10 trees each. Trees were on PG-1 rootstock.
[2]Grower-paid yield is the weight of harvested nuts for which the grower is paid. This yield is basically the CPC assessed weight minus the weight of the shells from closed shell and shelling stock.

Evaluation data from the Madera County Test plot is presented in Table 6. This data is relatively preliminary, representing only the first harvestable yield. As was true at the Kern County location, split nut percentages were higher for 'Lost Hills' and blank nut percentages were lower for 'Lost Hills' as compared to 'Kerman'. Nut weights were similar to 'Kerman'. Tables 7–18 show additional data on the yield of 'Lost Hills' as compared to both 'Kerman' (unpatented) and 'Golden Hills' (U.S. patent application Ser. No. 11/086,170).

TABLE 6

Nut characteristics for three advanced selections and 'Kerman' on 'PG-1' and 'UCB1' rootstock in a test plot located in southern Madera County, 2004

| Cultivar | split nut, % | adhering hull, % | blank nuts, % | loose shell and kernel, % | average nut weight[1], grams |
|---|---|---|---|---|---|
| 'Kerman' | 59.4 | 10.6 | 13.8 | 3.7 | 1.29 |
| 'Lost Hills' | 73.6 | 11.2 | 5.2 | 0.9 | 1.19 |

[1]Based on 50 nut samples.

TABLE 7

ANOVA for total yield (CCP assessed weight). Years, varieties, and interactions were significant.

| | DF | Sum of Squares | Mean Square | F-Value |
|---|---|---|---|---|
| year | 2 | 11657142.111 | 5828571.056 | 51.397 |
| variety | 2 | 1888152.111 | 944076.056 | 8.325 |
| year * variety | 4 | 1710508.889 | 427627.222 | 3.771 |
| Residual | 9 | 1020624.500 | 113402.722 | |

| | P-Value | Lambda | Power |
|---|---|---|---|
| year | <.0001 | 102.794 | 1.000 |
| variety | .0090 | 16.650 | .880 |
| year * variety | .0455 | 15.083 | .668 |
| Residual | | | |

TABLE 8

Total yield means table (lbs/acre CCP assessed weight) for varieties x years.

| | Count | Mean | Std. Dev. | Std. Err. |
|---|---|---|---|---|
| 2002, Kerman | 2 | 1593.500 | 88.388 | 62.500 |
| 2002, Lost Hills | 2 | 1707.500 | 67.175 | 47.500 |
| 2002, Golden Hills | 2 | 1762.500 | 540.937 | 382.500 |

TABLE 8-continued

Total yield means table (lbs/acre CCP assessed weight) for varieties x years.

| | Count | Mean | Std. Dev. | Std. Err. |
|---|---|---|---|---|
| 2003, Kerman | 2 | 1081.500 | 55.861 | 39.500 |
| 2003, Lost Hills | 2 | 2185.000 | 537.401 | 380.000 |
| 2003, Golden Hills | 2 | 2048.500 | 386.787 | 273.500 |
| 2004, Kerman | 2 | 3032.000 | 52.326 | 37.000 |
| 2004, Lost Hills | 2 | 2998.000 | 345.068 | 244.000 |
| 2004, Golden Hills | 2 | 4276.000 | 390.323 | 276.000 |

TABLE 9

Mean differences for yield (CCP assessed weight), protected LSDs, and Scheffe tests (5% significance) for varieties. 'Golden Hills' had significantly higher yield than 'Kerman' at the 1% significance level. 'Lost Hills' had higher yields than 'Kerman', but only at the 7.3% level and lower yield than 'Golden Hills', also at the 7% level. S denotes significant difference at 5%.

| | Mean Diff. | Crit. Diff. | P-Value | |
|---|---|---|---|---|
| LSD | | | | |
| Golden Hills, Kerman | 793.333 | 439.819 | .0028 | S |
| Golden Hills, Lost Hills | 398.833 | 439.819 | .0705 | |
| Kerman, Lost Hills | −394.500 | 439.819 | .0730 | |
| Scheffe | | | | |
| Golden Hills, Kerman | 793.333 | 567.273 | .0090 | S |
| Golden Hills, Lost Hills | 398.833 | 567.273 | .1780 | |
| Kerman, Lost Hills | −394.500 | 567.273 | .1836 | |

TABLE 10

ANOVA for split nut yields. Years, varieties, and interactions were significant.

| | DF | Sum of Squares | Mean Square | F-Value |
|---|---|---|---|---|
| year | 2 | 11502633.333 | 5751316.667 | 59.748 |
| variety | 2 | 1966566.333 | 983283.167 | 10.215 |
| year * variety | 4 | 2154286.333 | 538571.583 | 5.595 |
| Residual | 9 | 866340.500 | 96260.056 | |

| | P-Value | Lambda | Power |
|---|---|---|---|
| year | <.0001 | 119.495 | 1.000 |
| variety | .0048 | 20.430 | .938 |
| year * variety | .0153 | 22.380 | .848 |
| Residual | | | |

TABLE 11

Split nut yields means table (lbs/acre) for varieties x years.

| | Count | Mean | Std. Dev. | Std. Err. |
|---|---|---|---|---|
| 2002, Kerman | 2 | 1355.000 | 171.120 | 121.000 |
| 2002, Lost Hills | 2 | 1474.000 | 65.054 | 46.000 |
| 2002, Golden Hills | 2 | 1677.500 | 478.711 | 338.500 |
| 2003, Kerman | 2 | 641.000 | 106.066 | 75.000 |
| 2003, Lost Hills | 2 | 2016.500 | 504.167 | 356.500 |
| 2003, Golden Hills | 2 | 1484.000 | 216.375 | 153.000 |
| 2004, Kerman | 2 | 2725.500 | .707 | .500 |
| 2004, Lost Hills | 2 | 2707.500 | 327.390 | 231.500 |
| 2004, Golden Hills | 2 | 3968.500 | 429.214 | 303.500 |

TABLE 12

Mean differences, protected LSDs, and Scheffe tests (5% significance) for varieties (split nut yields). Both 'Lost Hills' and 'Golden Hills' had significantly higher yields of split nuts than 'Kerman' at the 1% significance level. S denotes significant difference at 5%.

| | Mean Diff. | Crit. Diff. | P-Value | |
|---|---|---|---|---|
| LSD | | | | |
| Golden Hills, Kerman | 802.833 | 405.215 | .0015 | S |
| Golden Hills, Lost Hills | 310.667 | 405.215 | .1169 | |
| Kerman, Lost Hills | −492.167 | 405.215 | .0226 | S |
| Scheffe | | | | |
| Golden Hills, Kerman | 802.833 | 522.641 | .0051 | S |
| Golden Hills, Lost Hills | 310.667 | 522.641 | .2732 | |
| Kerman, Lost Hills | −492.167 | 522.641 | .0645 | |

TABLE 13

ANOVA for % split nuts (transformed data). Years, varieties, and interactions were significant.

| | DF | Sum of Squares | Mean Square | F-Value | P-Value | Lambda | Power |
|---|---|---|---|---|---|---|---|
| year | 2 | 11.297 | 5.649 | 23.416 | .0003 | 46.832 | 1.000 |
| variety | 2 | 5.627 | 2.813 | 11.663 | .0032 | 23.325 | .964 |
| year * variety | 4 | 11.524 | 2.881 | 11.943 | .0012 | 47.771 | .995 |
| Residual | 9 | 2.171 | .241 | | | | |

TABLE 14

Mean % split nuts (lbs/acre) for varieties x years - untransformed data.

| | Count | Mean | Std. Dev. | Std. Err. |
|---|---|---|---|---|
| 2002, Kerman | 2 | 84.866 | 6.031 | 4.265 |
| 2002, Lost Hills | 2 | 86.317 | .414 | .293 |
| 2002, Golden Hills | 2 | 95.507 | 2.152 | 1.521 |
| 2003, Kerman | 2 | 59.602 | 12.886 | 9.112 |
| 2003, Lost Hills | 2 | 92.241 | .387 | .274 |
| 2003, Golden Hills | 2 | 72.743 | 3.172 | 2.243 |
| 2004, Kerman | 2 | 89.904 | 1.528 | 1.081 |
| 2004, Lost Hills | 2 | 90.280 | .529 | .374 |
| 2004, Golden Hills | 2 | 92.737 | 1.573 | 1.112 |

TABLE 15

Mean differences, protected LSDs, and Scheffe tests (5% significance) for varieties (% split nuts - transformed data). Both 'Lost Hills' and 'Golden Hills' had significantly higher yields of split nuts than 'Kerman' at the 1+% significance level. 'Lost Hills' and 'Golden Hills' were not significantly different with respect to split nut percentages. S denotes significant difference at 5%.

| | Mean Diff. | Crit. Diff. | P-Value | |
|---|---|---|---|---|
| LSD | | | | |
| Golden Hills, Kerman | .051 | .041 | .0187 | S |
| Golden Hills, Lost Hills | −.016 | .041 | .4090 | |
| Kerman, Lost Hills | −.067 | .041 | .0047 | S |
| Scheffe | | | | |
| Golden Hills, Kerman | .051 | .041 | .0187 | S |
| Golden Hills, Lost Hills | −.016 | .041 | .4090 | |
| Kerman, Lost Hills | −.067 | .041 | .0047 | S |

TABLE 16

ANOVA for grower paid yield. Years, varieties, and interactions were significant.

| | DF | Sum of Squares | Mean Square | F-Value |
|---|---|---|---|---|
| year | 2 | 11536201.444 | 5768100.722 | 56.150 |
| variety | 2 | 1925492.111 | 962746.056 | 9.372 |
| year * variety | 4 | 1888457.889 | 472114.472 | 4.596 |
| Residual | 9 | 924545.000 | 102727.222 | |

| | P-Value | Lambda | Power |
|---|---|---|---|
| year | <.0001 | 112.299 | 1.000 |
| variety | .0063 | 18.744 | .916 |
| year * variety | .0269 | 18.383 | .763 |
| Residual | | | |

TABLE 17

Grower paid yield means table (lbs/acre) for varieties x years.

| | Count | Mean | Std. Dev. | Std. Err. |
|---|---|---|---|---|
| 2002, Kerman | 2 | 1474.000 | 130.108 | 92.000 |
| 2002, Lost Hills | 2 | 1591.000 | 66.468 | 47.000 |
| 2002, Golden Hills | 2 | 1720.500 | 509.824 | 360.500 |
| 2003, Kerman | 2 | 861.500 | 24.749 | 17.500 |
| 2003, Lost Hills | 2 | 2099.500 | 519.723 | 367.500 |
| 2003, Golden Hills | 2 | 1766.500 | 301.935 | 213.500 |
| 2004, Kerman | 2 | 2875.500 | 21.920 | 15.500 |
| 2004, Lost Hills | 2 | 2853.000 | 336.583 | 238.000 |
| 2004, Golden Hills | 2 | 4122.500 | 409.415 | 289.500 |

TABLE 18

Mean differences, protected LSDs, and Scheffe tests (5% significance) for varieties (grower paid yield). Both 'Lost Hills' and 'Golden Hills' had significantly higher grower paid yield of split nuts than 'Kerman' at the 5% significance level. 'Golden Hills' had higher grower paid yield than 'Lost Hills' at the 9% significance level. S denotes significant difference at 5%.

| | Mean Diff. | Crit. Diff. | P-Value | |
|---|---|---|---|---|
| LSD | | | | |
| Golden Hills, Kerman | 799.500 | 418.605 | .0019 | S |
| Golden Hills, Lost Hills | 355.333 | 418.605 | .0870 | |
| Kerman, Lost Hills | −444.167 | 418.605 | .0399 | S |
| Scheffe | | | | |
| Golden Hills, Kerman | 799.500 | 539.912 | .0064 | S |
| Golden Hills, Lost Hills | 355.333 | 539.912 | .2133 | |
| Kerman, Lost Hills | −444.167 | 539.912 | .1079 | |

Chilling requirement: This variety has less of a chilling requirement for dormancy as compared to 'Kerman' resulting in more uniform spring foliation, flowering, pollination and nut maturity at harvest.

Disease resistance and susceptibility: Earlier harvest resulted in significantly less navel orangeworm damage (0.0% vs. 9.3%). This is an important characteristic since nut damage on the tree is associated with aflatoxin contamination.

Usage: The nuts are primarily sold as a dry "in shell" product for direct consumption at the retail level. They made be sold either "salted" or "unsalted". They are marketed either in packages or are sold in bulk. Small quantities may be used in confections or ice cream. The shipping quality of the nut is excellent, and is similar to kerman when the husk is removed and the nut is dried. The nut maybe stored dry (<6% moisture) at room temperature for up to one year, before exhibiting off-type or stale flavor.

'Lost Hills' is a female tree with a harvest date 2 to 4 weeks earlier than 'Kerman', which is the industry standard. 'Lost Hills' produces a higher percentage of split, edible nuts than 'Kerman' in all years, especially in 2003 when split percentages for 'Kerman' were very poor. Nut size is larger than 'Kerman', but weight is similar. The earlier harvest date will permit growers to extend their harvest period and reduce competition for scarce harvesting resources and may reduce disease in the northern production areas of the state by permitting an earlier harvest before fall rains. The cultivar requires less chilling than 'Kerman', which improves uniformity of foliation, bloom, nut set, nut fill, and uniformity of nut maturity at harvest in years with insufficient chilling for 'Kerman'.

What we claim is:

1. A new and distinct variety of pistachio tree substantially as shown and described herein.

* * * * *

'Kerman'

'Lost Hills'